United States Patent [19]

Boomgaarden et al.

[11] Patent Number: 4,829,844
[45] Date of Patent: May 16, 1989

[54] POWER ASSIST HANDLE

[75] Inventors: Jonathan C. Boomgaarden, Waukesha; Marlene R. A. Bandoian, Wales; David W. Ambrose, Waukesha, all of Wis.

[73] Assignee: General Electric Company, Milwaukee, Wis.

[21] Appl. No.: 125,658

[22] Filed: Nov. 25, 1987

[51] Int. Cl.4 ............................................. G05G 1/00
[52] U.S. Cl. ...................................... 74/470; 74/469; 180/6.48; 180/6.5
[58] Field of Search ................. 318/628; 74/470, 469, 74/471 XY, 471 R, 491, 488, 489, 496; 180/6.48, 6.5, 6.24, 6.28, 6.32, 19.1–19.3, 315, 332, 333

[56] References Cited

U.S. PATENT DOCUMENTS

| | | | |
|---|---|---|---|
| 4,036,321 | 7/1977 | Habiger | 74/471 XY |
| 4,367,373 | 1/1983 | McDaniel et al. | 74/471 XY |
| 4,697,661 | 10/1987 | Pajerski et al. | 74/471 R |

Primary Examiner—William M. Shoop, Jr.
Assistant Examiner—Brian Young
Attorney, Agent, or Firm—Douglas E. Stoner; Mark L. Mollon

[57] ABSTRACT

A power assist handle for providing control signals to a servo mechanism includes a spring-guided means of allowing motion of an input handle in only two directions in a configuration which has almost no friction between stationary and moving parts. Motion is sensed by a pair of Hall-effect sensors, each of which provides a signal output proportional to the displacement of the input handle in a respective orthogonal direction. The sensors and associated permanent magnets are arranged so that each is sensitive in one of the two directions and insensitive in the other.

5 Claims, 2 Drawing Sheets

POWER ASSIST HANDLE

BACKGROUND OF THE INVENTION

The present invention relates in general to a power assist handle for generating control signals and, more specifically, to a power assist handle for diagnostic imaging equipment, such as a spot-film device.

Two-axis (i.e., four-way) power assist handles provide motion along two orthogonal axes and include a means of sensing the motion. A signal indicating the motion is generated by the sensors and provided to a power assist device, such as a servo system for moving the device to which the handle is attached.

Two-axis power assist handles are commonly used on the movable portions of medical diagnostic equipment, such as an X-ray spot-film device used in connection with radiographic and fluoroscopic systems. The desired directions of motion for these devices are up-down and left-right. These motions should be independently achieved within the handle itself, and motion along each axis should be independently sensed. Motion on each axis should be achievable simultaneously and by applying force at any location of the handle.

Previous handle designs have accomplished the necessary functions by placing two sensors on a rigid support and using a member which forms the hand grip and encloses the support to push against a load- or displacement-sensing part of the sensors. For example, moving core transformers have been employed where handle motion changes the coil coupling. The voltage on the secondary winding or windings can be sensed to indicate handle motion. However, due to the small size of these coils, high frequency primary voltage is required which leads to high-cost components. Furthermore, this type of mechanism introduces friction which creates hysteresis in the control motion. This type of mechanism cannot prevent rotation about all three axes. Consequently, motion of the handle is dependent on the location at which the displacement force is applied.

Accordingly, it is a principal object of the present invention to provide a power assist handle having motion in only two directions, with no rotation about any axis.

It is another object of the present invention to substantially eliminate friction in a power assist handle.

It is a further object of the invention to provide sensors for a power assist handle each sensitive only to motion in one direction.

It is yet another object of the invention to provide a power assist handle using low-cost d.c. electronics.

It is yet another object of the invention to provide a power assist handle wherein displacement of the handle is essentially linear with applied load and wherein the handle has negligible hysteresis.

It is still another object of the invention to provide handle motion which is substantially independent of the location on the handle where displacement force is applied.

SUMMARY OF THE INVENTION

These and other objects are achieved in a power assist handle adapted for movement in first and second orthogonal directions which comprises a support member, a carriage assembly and a pair of resilient anchor springs. The carriage assembly includes first and second carriage members joined by a pair of resilient crossed springs at their proximal ends to form a flexure pivot allowing rotation of the carriage members in the plane of the orthogonal directions. The pair of resilient anchor springs are connected to the carriage assembly and to said support member each at a respective distal end of the first and second carriage members, such that the anchor springs are movable in substantially only one of the directions.

In a further embodiment of the power assist handle, the support member has a pair of apertures, and each carriage member has an aperture co-linearly aligned with a respective support member aperture. Each carriage member aperture has a diameter which is smaller than its respective support member aperture and all of the apertures have their axes substantially perpendicular to the first and second orthogonal directions. The housing member includes a pair of pins passing within the previously mentioned aligned apertures such that the carriage members are rotatable about the pins. The support member apertures act as mechanical stops for the carriage assembly motion.

In another aspect of the invention, the power assist handle comprises a fixed support member, a moving handle member, a pair of Hall-effect sensors and a pair of magnet means. The Hall-effect sensors are mounted to the support member. The pair of magnet means are each mounted on the handle member juxtaposed with a respective Hall-effect sensor. Each magnet means provides a linearly varying magnetic field in a respective one of the directions and a substantially constant magnetic field in the other direction.

BRIEF DESCRIPTION OF THE DRAWINGS

The novel features of the invention are set forth with particularity in the appended claims. The invention itself, however, both as to its organization and method of operation, together with further objects and advantages thereof, may best be understood by reference to the following description taken in conjunction with the accompanying drawings in which:

DETAILED DESCRIPTION OF THE INVENTION

Figure 1:
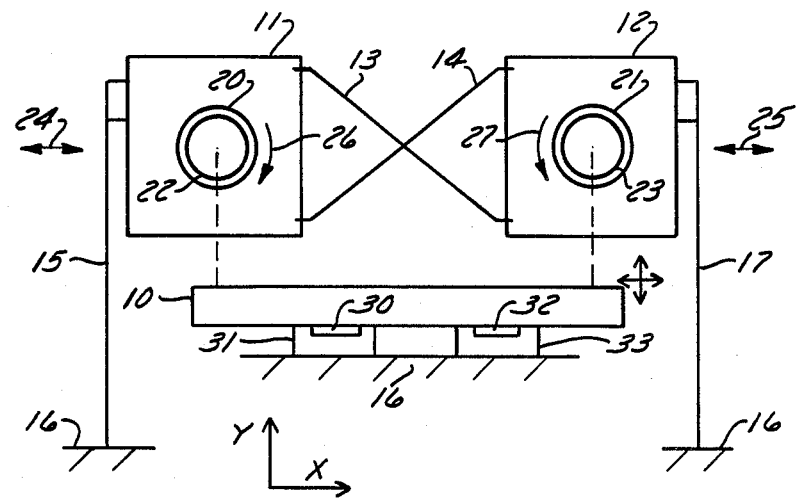
FIG. 1 is a block diagram for illustrating the principles of the invention.

FIG. 1 is a front block diagram of a mechanism for moving a handle 10 in the X and Y directions as indicated. The mechanism includes a carriage assembly comprising a pair of saddle blocks 11 and 12 joined by a pair of flat, resilient crossed springs 13 and 14 anchored at the proximal ends of saddle blocks 11 and 12. Springs 13 and 14 are not otherwise connected. Saddle blocks 11 and 12 are grounded to a fixed structure 16 (such as a spot-film device) by flat, resilient anchor springs 15 and 17, respectively. Apertures 20 and 21 in saddle blocks 11 and 12, respectively, each receives a pin 22 and 23, respectively, each connected to handle 10.

Resilient springs 13, 14, 15 and 17 are comprised of thin resilient sheets and are viewed edge in FIG. 1. Saddle blocks 11 and 12 are rotatable about pins 22 and 23, respectively.

The mechanism of FIG. 1 allows motion of handle 10 in only the X and Y directions and does not allow rotation of handle 10. The structure consisting of saddle blocks 11 and 12 and crossed springs 13 and 14 provides a rigid structure with respect to motion in the X direction. Thus, motion in the X direction of the carriage assembly and handle is provided by S-bending of anchor springs 15 and 17, as indicated by arrows 24 and 25.

If the carriage assembly were totally rigid, anchor springs 15 and 17 would prevent movement in the Y direction. However, the carriage assembly is in the form of a flexure pivot which allows saddle blocks 11 and 12 to be rotated about an axis in the vicinity of pins 22 and 23. Motion of saddle blocks 11 and 12 is constrained by crossed flexure pivot springs 13 and 14 to rotations about pins 22 and 23 which are substantially equal in magnitude but are in opposite directions. Thus, in response to a displacement force applied to handle 10 in the Y direction, saddle blocks 11 and 12 rotate about pins 22 and 23, flexing springs 13, 14, 15 and 17, and handle 10 is allowed to move in the Y direction. Rotation of saddle blocks 11 and 12 are in opposite directions as indicated by arrows 26 and 27.

Also shown in FIG. 1 are means for sensing the X and Y motion of handle 10. A first sensor for the Y direction includes a magnet 30 and a Hall-effect sensor 31. A sensor for the X direction includes a magnet 32 and a Hall-effect sensor 33. Each sensor 31 and 33 is separated from its respective magnet by a gap. These sensing elements are preferred since they are non-contacting and thereby eliminate friction. Magnet 30 provides a magnetic field which is linearly varying in the Y direction and which is substantially constant in the X direction. Magnet 32 provides a magnetic field which varies linearly in the X direction and which is substantially constant in the Y direction. Thus, each sensor 31 and 33 senses motion only in one direction.

Figure 2:
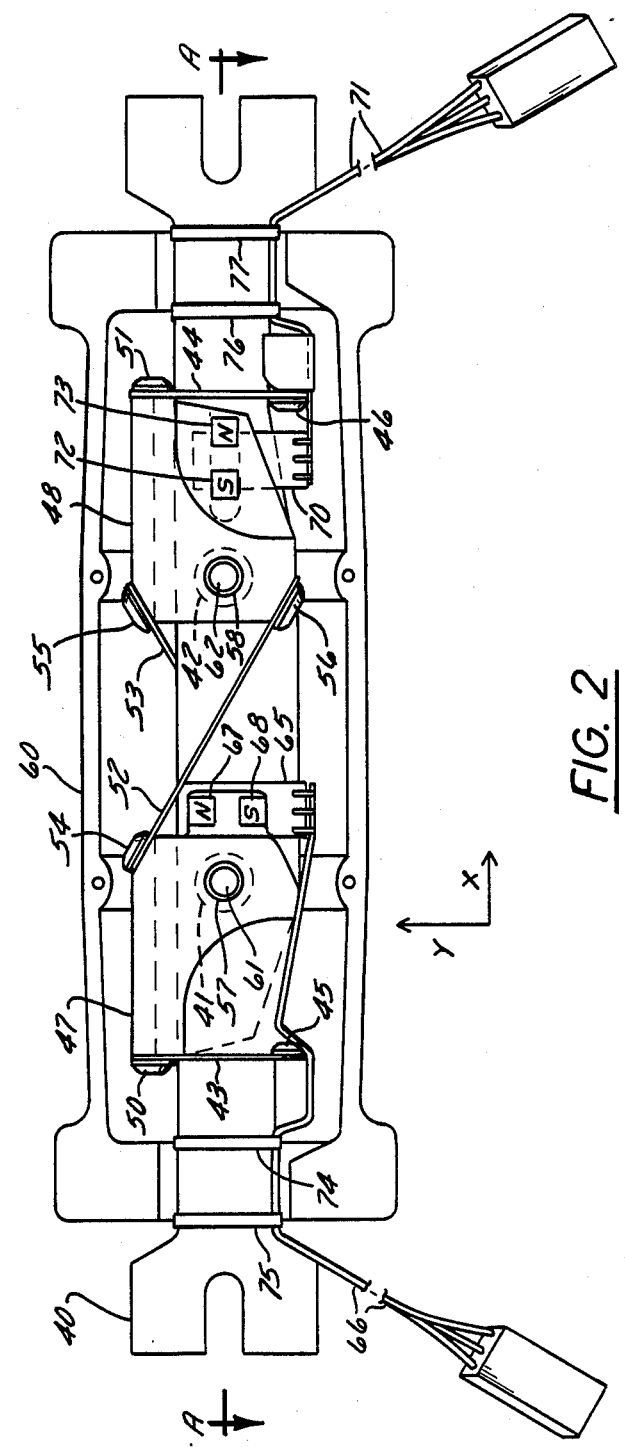
FIG. 2 is a front vertical cross section of a preferred embodiment of the invention.

Turning now to FIG. 2, a preferred embodiment of the invention is shown with the front half of its handle member removed. A support member 40 includes a pair of apertures 41 and 42 and is adapted to be connected in a fixed manner to the spot-film device or other device to which the power assist handle will be affixed. A pair of flat, resilient anchor springs 43 and 44 are fixed to support member 40 at connections 45 and 46. The free ends of springs 43 and 44 are fixed to carriage members 47 and 48 at connections 50 and 51, respectively. A flat, resilient crossed spring 52 is connected to carriage member 47 at fixed connection 54 and to carriage member 48 at fixed connection 56. A flat, resilient crossed spring 53 is connected to carriage member 48 at fixed connection 55 and to carriage member 47 at a fixed connection not shown. Carriage members 47 and 48 include apertures 57 and 58, respectively, which receive a pair of pins 61 and 62, respectively, which are connected to a handle or housing member 60.

The carriage assembly is thus supported relative to support member 40 by anchor springs 43 and 44 so that it can move substantially only in one direction, perpendicular to the thin dimension of anchor springs 43 and 44. Rotation of carriage members 47 and 48 about pins 61 and 62 provides motion in the other direction. These motions may be excited simultaneously or separately.

Also shown in FIG. 2 are sensors for detecting motion in the X and Y directions. The sensor for detecting motion in the Y direction includes a Hall-effect sensor 65 which is fixed on support member 40 and a pair of permanent magnets 67 and 68 which can be connected to carriage member 47 or to handle 60. Permanent magnets 67 and 68 have opposite poles facing sensor 65 across a gap therebetween. Thus, the flux seen by sensor 65 is substantially constant when permanent magnets 67 and 68 move in the X direction, while the flux seen by sensor 65 varies linearly when permanent magnets 67 and 68 move in the Y direction. A plurality of leads 66 connect sensor 65 to a servo mechanism (not shown) and are secured to support member 40 by straps 74 and 75. Likewise, a sensor 70 provides sensing of motion along the X axis by means of permanent magnets 72 and 73 oriented substantially perpendicular to the direction of magnets 67 and 68. A set of leads 71 for sensor 70 is secured to support member 40 by straps 76 and 77. It may be desirable to orient permanent magnets 72 and 73 along a line rotated by about 15 degrees in the counterclockwise direction from line A in order to account for the rotation of carriage member 48.

Motion occurs in both X and Y directions at both sensing elements. However, the elements are configured to only sense motion in one direction, since the magnetic field provided by a set of magnets is constant in one direction while it varies linearly in the orthogonal direction.

Figure 3:
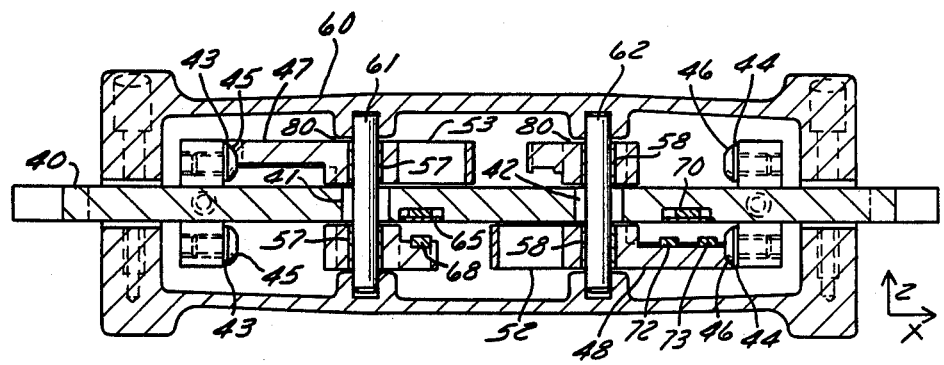
FIG. 3 is a horizontal cross section along the line A—A of FIG. 2.

The features of the invention will be further described with reference to FIG. 3 which is a horizontal cross section along line A—A of FIG. 2 with the front portion of the handle restored. Apertures 41 and 42 are shown in support member 40. Support member 40 is also shown to be extending longitudinally through carriage members 47 and 48. Thus, carriage members 47 and 48 include suitable bores for receiving support member 40. Also, anchor springs 43 and 44 contain portions extending vertically on either side of support member 40. For example, in a preferred embodiment, flat anchor springs 43 and 44 are U-shaped.

In the power-assist-handle structure of the invention, the only sliding friction contact is between pins 61 and 62 and carriage members 47 and 48. Since the normal force between these parts becomes negligible when no load is supplied to the handles, the structure is substantially free from hysteresis.

The structure permits motion in the X and Y directions, either simultaneously or separately, but prevents both motion along the Z axis and rotations about any axis. Maximum X and Y travel results when pins 61 and 62 contact support member apertures 41 and 42, respectively. Linear motion in the Z direction is limited by a small clearance 80 between the carriage members and the handle. This clearance also prevents rotation about the Y axis. Rotation about the X axis is limited by the clearance between pins 61 and 62 and carriage members 47 and 48, respectively, since the carriage members are connected to support member 40 by springs which are stiff in the lateral (i.e., Y) direction. Rotation is limited about the Z direction by the clearance between pins 61 and 62 and carriage members 47 and 48, respectively, since the carriage assembly prevents motion other than rotation within itself, and since tension and compression in anchor springs 43 and 44 result from the stiff connection between them and support member 40.

Due to the inability of the handle of the present invention to rotate about any axis, handle actuation is substantially not dependent on the location at which actuating force is applied.

The motion sensors of the invention provide a signal output which is proportional to the displacement of the handle. Motion is sensed in primarily only one direction for each sensor. The use of a non-contact sensor avoids the creation of unnecessary friction. Furthermore, Hall-effect sensors are easily implemented with low voltage, low cost d.c. electronics, thus avoiding the high expense of prior-art power assist handles.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed is:

1. A handle adapted for movement in first and second orthogonal directions comprising:
    a support member;
    a carriage assembly including first and second carriage members joined by a pair of resilient crossed springs at their proximal ends to form a flexure pivot allowing rotation of said carriage members in the plane of said orthogonal directions; and
    a pair of resilient anchor springs connecting said carriage assembly to said support member, each at a respective distal end of said first and second carriage members, such that said anchor springs are movable in substantially only one of said directions.

2. The power assist handle of claim 1 wherein said support member has a pair of apertures and wherein each of said carriage members has an aperture co-linearly aligned with a respective support member aperture, and each having a diameter smaller than its respective support member aperture, all of said apertures having their axes substantially perpendicular to said first and second orthogonal directions, said handle further comprising:
    a housing member including a pair of pins passing within a respective pair of aligned apertures such that said carriage members are rotatable about said pins.

3. The power assist handle of claim 1 wherein said first and second carriage members each includes a bore for receiving said support member.

4. A power assist handle adapted for movement in first and second orthogonal directions comprising:
    a fixed support member;
    a moving handle member movable in said first and second orthogonal directions;
    a pair of Hall-effect sensors mounted to said support member, each sensor being oriented to sense a magnetic field in a respective one of said first and second directions; and
    a pair of magnet means each mounted on said handle member juxtaposed with a respective Hall-effect sensor, each magnet means for providing a linearly varying magnetic field in a respective one of said directions and a substantially constant magnetic field in the other direction, such that each respective Hall-effect sensor is responsive to movement of said magnet means in only one direction.

5. The power assist handle of claim 4 wherein said pair of magnet means each comprises a pair of permanent magnets.

* * * * *